United States Patent [19]

Bonneyrat et al.

[11] Patent Number: 4,546,643
[45] Date of Patent: Oct. 15, 1985

[54] METHOD AND DEVICE FOR ANALYZING EFFLUENTS FOR THE DETECTION OF PEAKS

[75] Inventors: Alain M. Bonneyrat, Saint Martin du Tertre; Christian L. Lanclais, Domont, both of France

[73] Assignee: Gilson Medical Electronics (France), Villiers Le Bel, France

[21] Appl. No.: 577,629

[22] PCT Filed: Jun. 2, 1983

[86] PCT No.: PCT/FR83/00107
§ 371 Date: Jan. 23, 1984
§ 102(e) Date: Jan. 23, 1984

[87] PCT Pub. No.: WO83/04325
PCT Pub. Date: Jun. 2, 1983

[30] Foreign Application Priority Data

Jun. 3, 1982 [FR] France ............................... 82/09675

[51] Int. Cl.⁴ ............................................ G01N 31/08
[52] U.S. Cl. .................................. 73/61.1 C; 364/498
[58] Field of Search ........................ 73/61.1 C, 23.1; 364/496, 497, 498, 499, 723

[56] References Cited

FOREIGN PATENT DOCUMENTS 1339510 9/1963 France .

OTHER PUBLICATIONS

Anderson et al., *Computer Analysis of Unresolved Non-Gaussian Gas Chromatograms by Curve-Fitting*, in Anal. Chem., vol. 42(4), pp. 434–440, Apr. 1970.
Burke et al., *Use of a Dedicated Computer for Real-Time Control of Gas Chromatographic Measurements*, in Journ. of Chrom. Sci., vol. 8, pp. 39–45, Jan. 1970.

*Primary Examiner*—Stewart J. Levy
*Assistant Examiner*—Joseph W. Roskos
*Attorney, Agent, or Firm*—Mason, Kolehmainen, Rathburn & Wyss

[57] ABSTRACT

The output signal of an effluent detector, disposed, for example, downstream of a liquid phase chromatography column, is digitalized and then compared to a LEVEL signal, fixed in relation to the base line of the detected signal, plus a deviation value (LO). A slope threshold is defined. As long as the slope of the detected signal is below the threshold, the pilot signal follows the detected signal. When the slope of the detected signal is higher than the threshold, a peak has occurred, and the value of the pilot signal locked, at least during a pre-established time. Thereafter the pilot signal resumes its evolution substantially parallel with the base line. This enables an outstanding detection of the useful peaks in the analysis of effluents.

10 Claims, 6 Drawing Figures

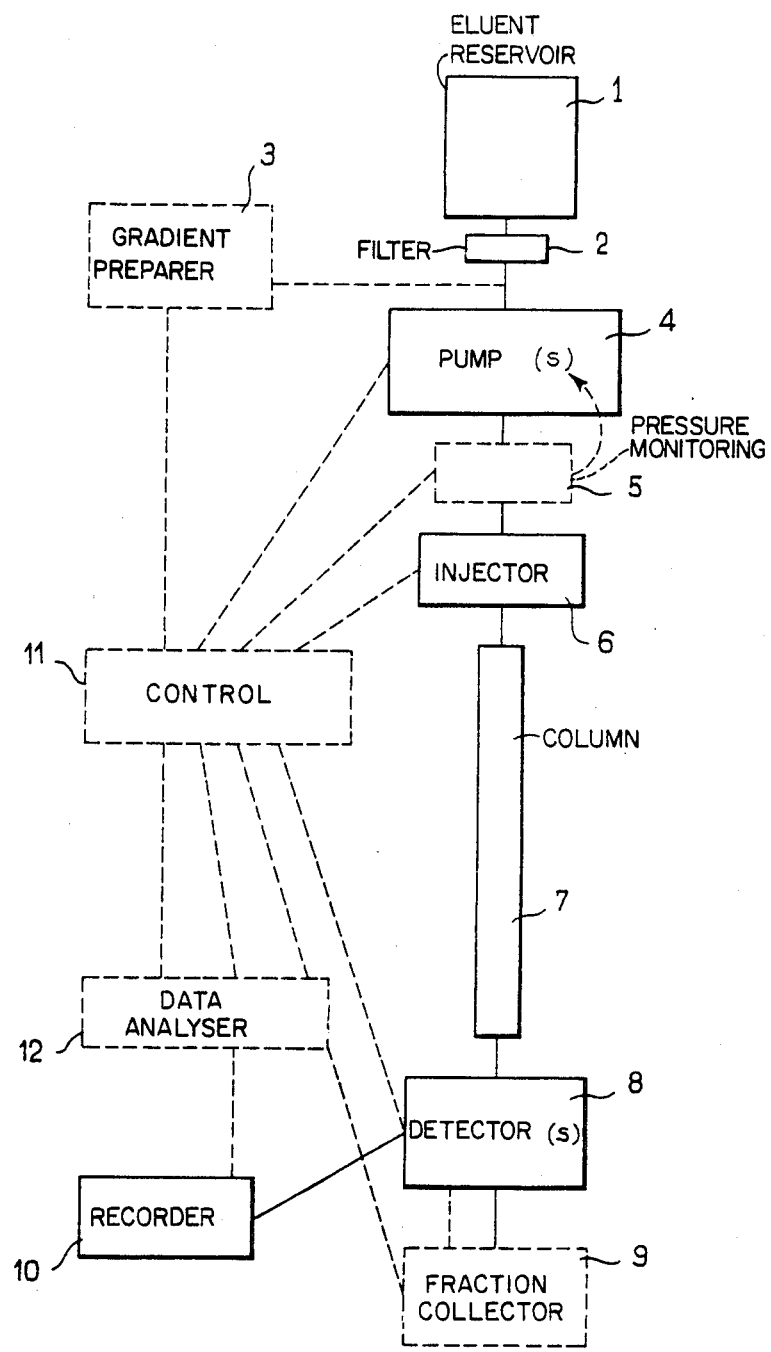
FIG_1

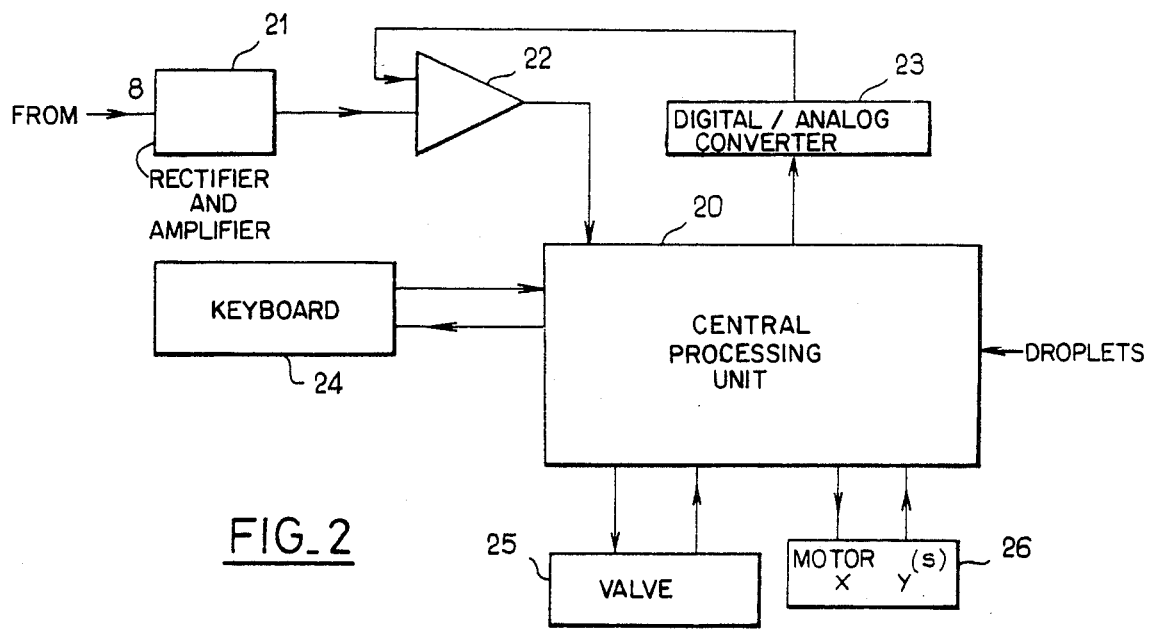
FIG_2
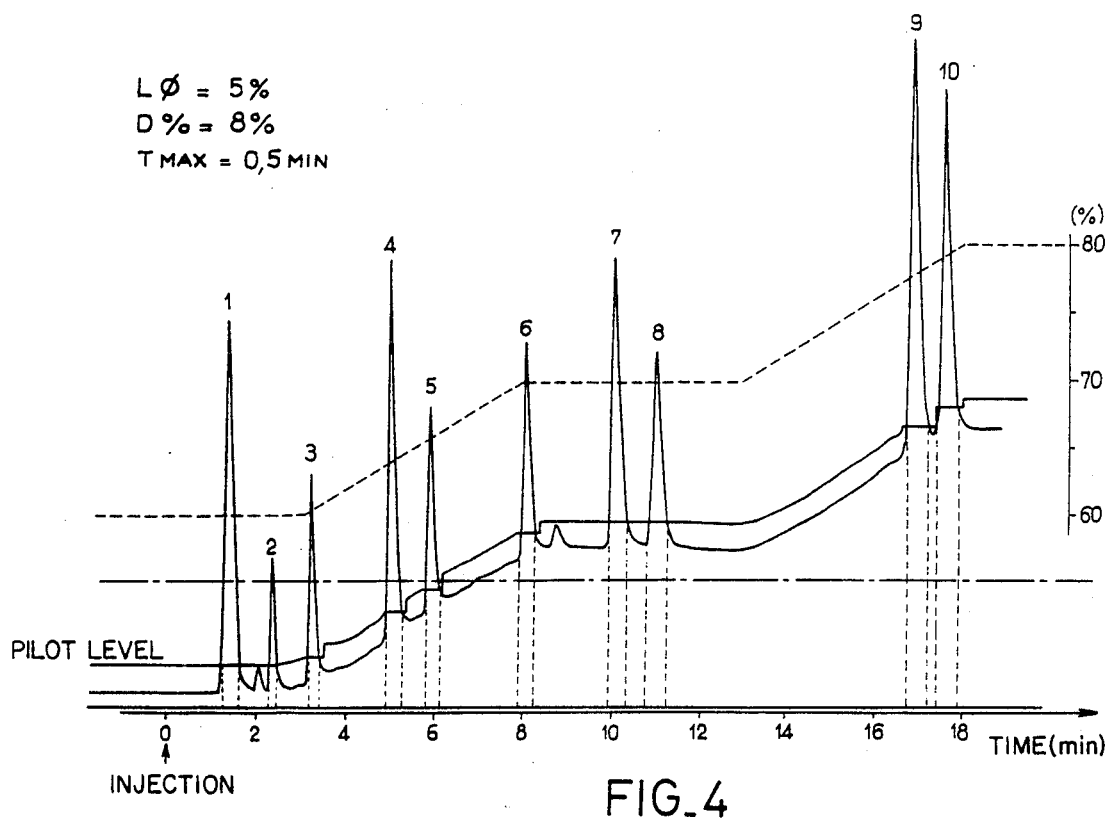
FIG_4

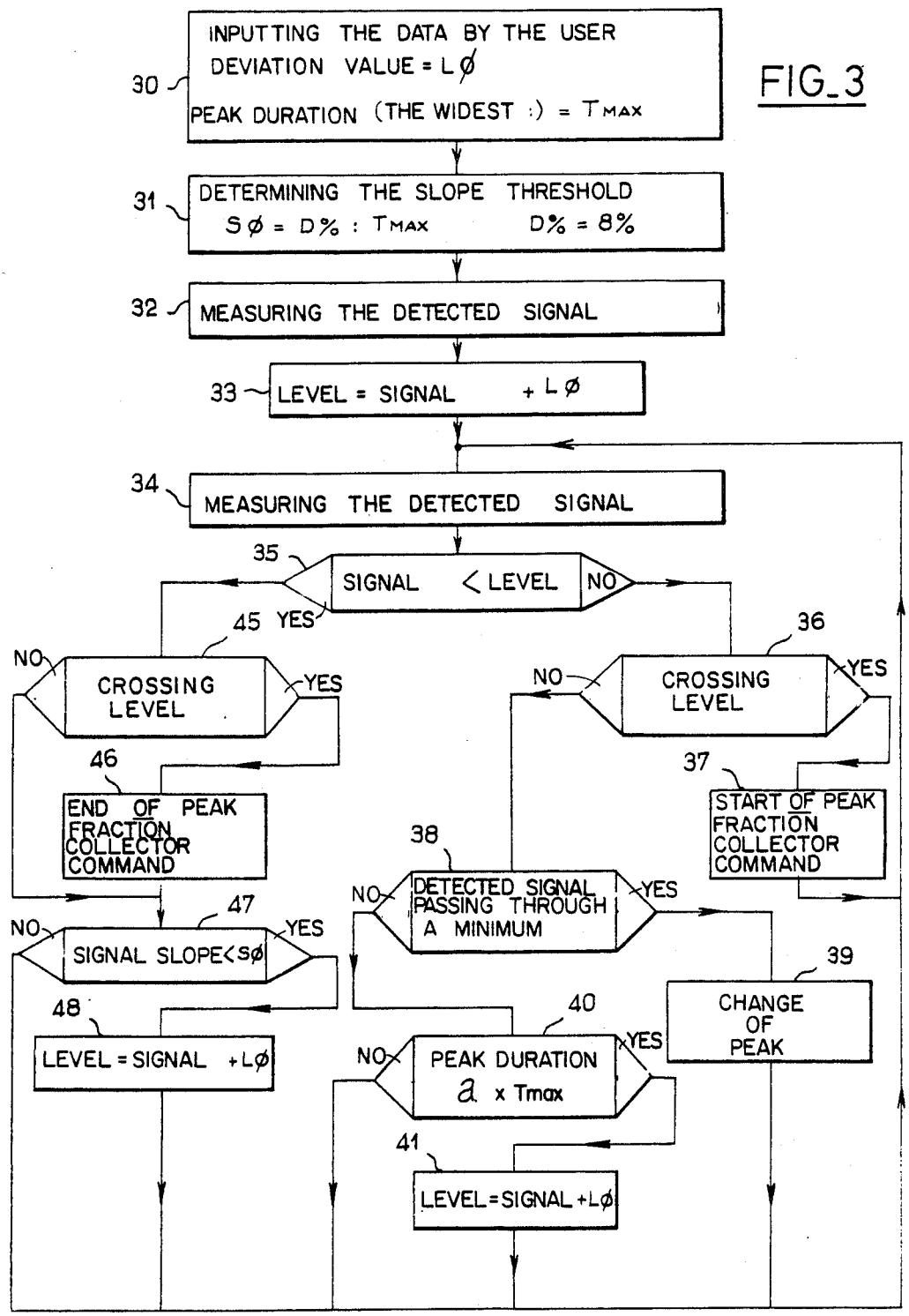

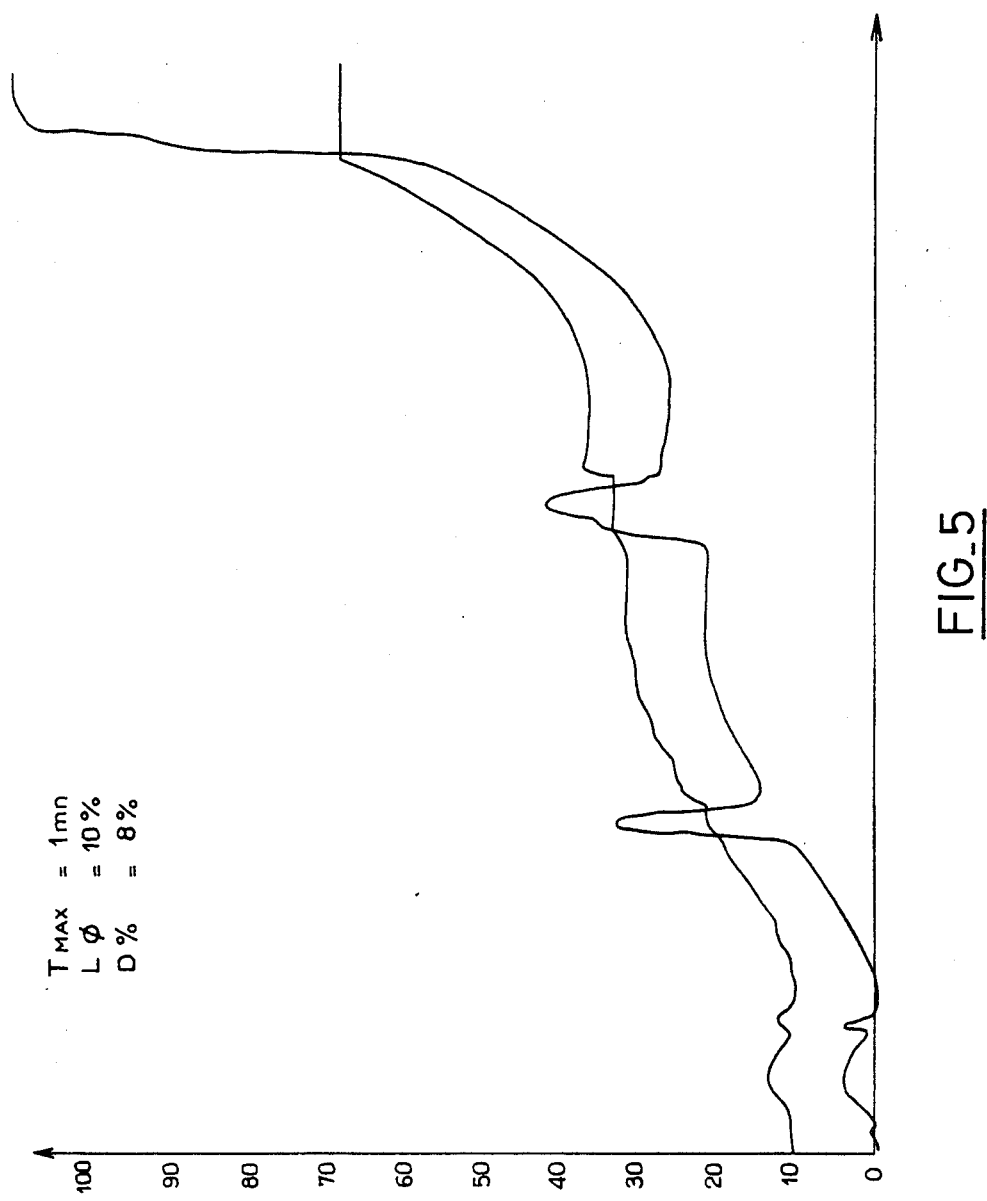
FIG_5

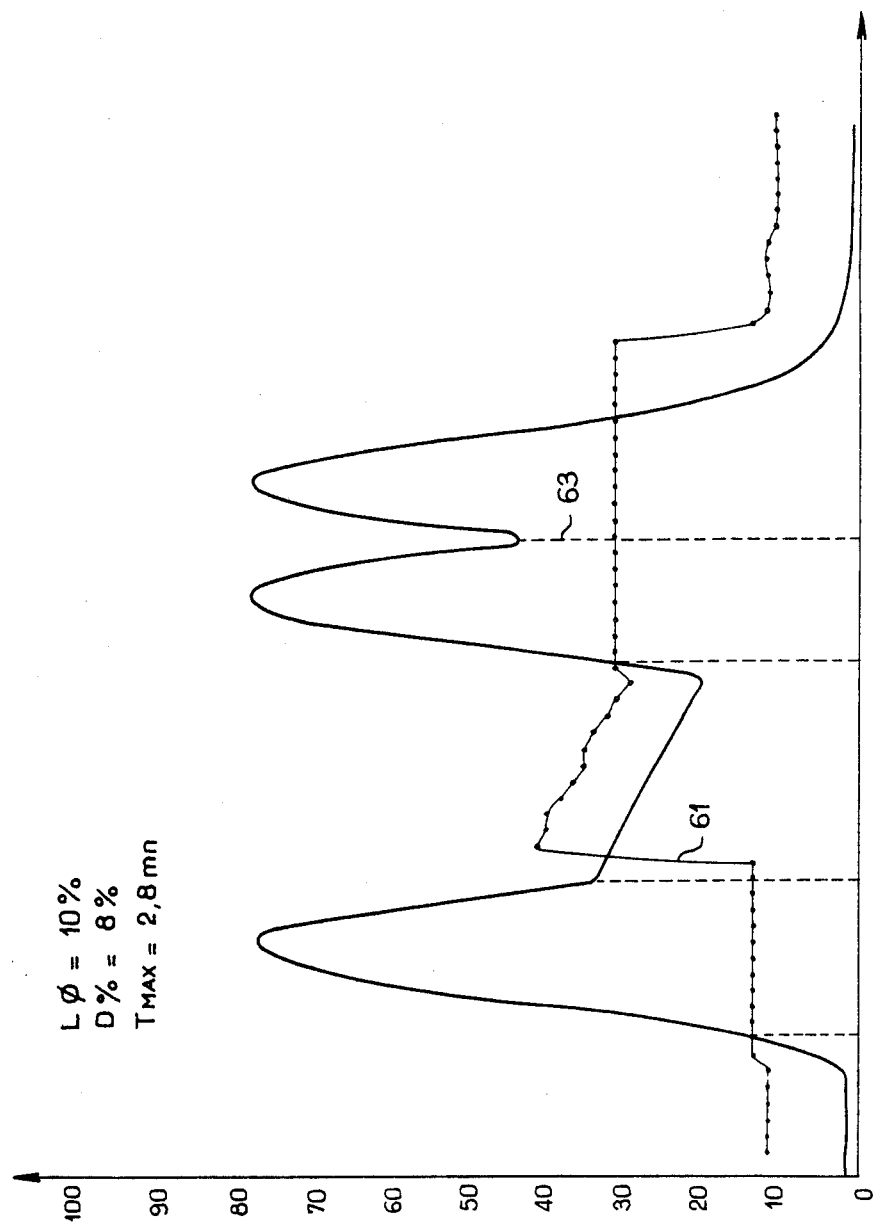
FIG._6

METHOD AND DEVICE FOR ANALYZING EFFLUENTS FOR THE DETECTION OF PEAKS

The invention relates to the analysis of effluents and more particularly, but not exclusively, is concerned with liquid phase chromatography.

In this particular field an eluent and a sample to be analysed are passed through a chromatography column. The eluent entrains various constituents of the sample selectively in the column.

At the outlet of the column, the effluent is subjected to the detection of a physical and/or chemical property, thus enabling the passage of the interesting constituents of the sample to be plotted. Detection is performed as a function of time, and supplies an analog electric signal.

The electrical signal can be regarded as comprising a "base line" having peaks, certain of which correspond to interesting constituents of the sample (useful peaks). The other peaks represent artefacts.

Any detection of a useful peak is generally accompanied by selective sampling of the effluent by means of an apparatus known as a fraction collector.

It is desirable to detect useful peaks automatically. Various techniques have been suggested for this purpose.

In the simplest, a constant threshold value is defined, slightly above the baseline. This method, which is quite suitable for certain applications, is in general not completely satisfactory: in difficult cases, the threshold must be made very low, so that an excessive number of useless samplings must be carried out.

It has therefore been proposed to take into account the slope of the detected signal, to plot the start and finish of peaks on it, as well as the minimum values between two closely adjoining slopes. There again, the technique is not entirely satisfactory.

Indeed, particularly in chromatography with a multi-component eluent with a concentration gradient the level of the baseline develops fairly quickly, thus rendering the aforementioned peak-detecting techniques inaccurate.

The present invention aims to provide a solution for these problems.

The invention provides a method of analysing effluents, in which:

(a) a physical and/or chemical property of the effluent is detected as a function of time, in the form of an electric signal, the electric signal detected comprising a baseline having peaks, certain of which represent useful information concerning the effluent;

(b) the detected signal is analysed, more particularly according to its slope, with a view to selecting useful peaks in it.

According to the invention the analytical stage (b) comprises the following operations:

(b1) defining a deviation value (L$\phi$) and a slope threshold (S$\phi$);

(b2) Comparing the slope of the detected signal with the threshold value (S$\phi$);

(b3) having the pilot signal evaluated from a value equal to the detected signal, plus the deviation value (L$\phi$), if the slope of the detected signal is lower than the threshold;

(b4) limiting the development of the pilot signal when the slope of the detected signal is higher than the threshold;

(b5) adopting as a useful peak those consecutive values of the detected signal which exceed the level of the pilot signal.

Preferably operation (b4) consists in freezing the pilot signal when the slope of the detected signal is higher than the threshold value (S$\phi$).

Very advantageously when the slope of the detected signal becomes lower than the threshold value (S$\phi$) again, the preceding value of the pilot signal is then resumed if the duration of exceeding the threshold was less than the selected duration (TMAX), or in the contrary case, a start is made again from a value equal to the sum of the detected signal and the deviation value (L$\phi$).

According to another aspect of the invention the deviation value (L$\phi$) and a selected duration (TMAX) can be defined by the user, the slope threshold (S$\phi$) being defined as the ratio between a pre-established quantity and the selected duration.

Preferably the passage of the detected signal through a minimum is also detected, thus defining any change in useful peak.

In practice, for the majority of applications the process is completed by an operation (c) consisting in sampling the effluent at least during a useful peak.

The invention also provides a fraction detecting and/or collecting device for analysing effluents, which comprises means for performing the aforedescribed method.

Other features and advantages of the invention will become apparent from a reading of the detailed description which follows and examination of the accompanying drawings, in which:

FIG. 1 illustrates diagramatically the general structure of an installation for liquid phase chromatography;

FIG. 2 illustrates highly diagramatically the main electronic elements adapted to be incorporated in the fraction detecting or collecting device shown in FIG. 1;

FIG. 3 is an operational flowsheet of the electronic means according to the invention; and FIGS. 4 to 6 show different detected signal and pilot signal curves obtained according to the invention.

The minimum structure of a liquid phase chromatography installation comprises an eluent reservoir 1 followed by a filter device 2. After that, one or more pumps 4 feed, if necessary via a pressure monitoring device 5, an injector 6 adapted to introduce the eluent into a chromatography column 7. The sample to be analysed is injected, for example by means of a syringe, either at the level of the injector 6, or more directly at the head of the column 7.

The effluents arriving as a function of time at the column outlet are analysed by one or more detectors 8. Usually a chart recorder 10 is associated with the detector 8.

As already stated, the detectors 8 detect a physical and/or chemical property of the effluent as a function of time, in the form of an electric signal. The electric detected-signal is thus rendered visible by the recorder 10 and, in general, comprises a baseline having peaks certain of which represent useful information about the effluent.

In very many applications the detector 8 is followed by a device 9 known as a fraction collector which has a grid of receiving tubes. It is associated with a sampling device adapted to introduce the effluents successively arriving at the column outlet into different tubes in a pre-established order.

Analysis is thus ultimately performed on the basis of the information supplied by recorder 10, and, if necessary, the samples available in an orderly and recognisable manner in the fraction collector 9.

It has become more and more usual to employ not a pure eluent, but an eluent formed by a mixture whose concentration is varied during chromatography. This is effected by an apparatus called a gradient preparer 3 which controls pumps 4, at least two pumps being provided in this embodiment which are associated with the same reservoir 1 and filter 2.

Lastly, nowadays the installation is completed by a (usually electronic) general control device 11 (FIG. 1). To this a data analyser 12 is added which is adapted to interact with the recorder and the fraction collector 9.

In practice the data analyser 12 is often incorporated either in the detector or in the fraction collector, the recorder also generally forming part of one or the other of these devices.

FIG. 2 shows the general electric circuit of an analytical device suitable for chromatography. A rectifying and amplifying device 21 is connected to the output of the detector 8 (FIG. 1). Rectification is necessary, since certain types of detection supply peaks which can be either negative or positive. The output of the amplifier-rectifier 21 is applied to an amplifier-comparator 22 whose output is applied to a central processing unit 20, which can regroup the devices 11 and 12 shown in FIG. 1. Amongst other things, the central processing unit generates a binary signal which is applied to a digital-analog converter 23, which then delivers a corresponding analog signal to the other input of the comparator 22. When the output signal of the amplifier-rectifier 21 becomes equal to the binary value defined by the central processing unit, the latter then assumes that such binary value numerically represents the analog value available at the output of the amplifier-rectifier 21, and stores that value.

A keyboard device 24 is also provided which enables different working data to be introduced into the central unit 20.

Lastly, the central unit 20 receives information from the fraction collector 9 to enable it to know, for example, whether the maximum number of droplets of effluents admitted into a particular tube has been reached. Via interfaces 25 and 26 the central unit 20 also controls the three-way valve devices and the displacement motors associated with the fraction collector, since the fraction collector will have to displace a distributing head above the aforementioned array of tubes, and suitably control such head so that the effluent sampled actually drops into the selected tube, or else is rejected to waste via the three-way valve.

Instead of defining the filling of the fraction collector by a number of droplets, of course the time during which the sample is transferred to a particular tube can be limited in a pre-determined manner.

The objective is to ensure that each useful peak of the effluents available at the outlet from the chromatography column enters a particular tube or number of tubes, if the duration of the peak is too long for only one tube to be suffice.

Operations according to the invention are stored in the central unit 20 and are used for processing the detected signal, sampled digitally in the manner stated hereinbefore.

FIG. 3 shows these operations in the form of a flow-sheet.

The first stage 30 in FIG. 3 consists in the inputting of the data by the user, by means of the keyboard 24. The data comprises at least one deviation value $L\phi$ and the widest peak duration TMAX.

It will be noted that the digital-analog converter 23 in FIG. 2 has a full scale. Internally the central processing unit 20 defines an upper limit in the form of a percentage of the full scale. Such percentage has the reference D% (8% for example).

The following stage 31 in FIG. 3 consists in determining the slope threshold from the value D%, and also the maximum duration TMAX inputted by the user. The ratio between D% and TMAX has the reference $S\phi$.

The following stage of the operation of the central processing unit 20 (FIG. 3) is the stage 32, consisting in measuring the detected signal, in the manner disclosed hereinbefore: the central unit successively generates increasing digital values which are converted into analog form by the device 23 and applied to the comparator 22. At the moment of equality with the input signal the latter is given a digital value equal to that which was delivered to the device 23 at the moment of equality.

Then comes the stage 33, which defines the current operation of the apparatus and is represented by the fact that a pilot signal is defined which is denoted LEVEL and represents the value of the detected signal, which is denoted SIGNAL+$L\phi$.

The stage 33 therefore enables the initial value of the pilot signal to be defined.

The stage 34 is then inscribed in the start of a loop which will define the continuation of the operation. The stage 34 consists in a fresh measurement of the detected signal, just like stage 32. The following stage 35 examines whether the detector signal is lower than the level of the pilot signal. If it is higher than the latter, the stage 36 is a test which determines whether this constitutes a crossing of the level of the pilot signal which has just been carried out. If so, stage 37 establishes that this is the start of the peak, and a command is given corresponding to the fraction collector to initiate a sampling of the effluents. A return is then made to 34.

If the stage 36 gave a "no" output, it would be because a peak was taking place. The test 38 examines whether the detected signal is passing through a minimum. If so, the stage 39 establishes a change of peak and consequently commands the fraction collector to pass on to a fresh tube.

If not, the output of stage 38 then passes to a test 40 which examines whether the duration of the peak is equal to a selected fraction of the duration TMAX defined by the user. If this condition of exceeding the duration is not verified, a return is made directly to the stage 34. If, on the contrary, the condition is verified, the stage 41 updates the value of the LEVEL signal, to establish the latter now at the current value of the detected signal, plus $L\phi$. A return is then made to stage 34.

It now remains to examine the "yes" output of the test 35. This output indicates that the detected signal remains lower than the level of the pilot signal. The stage 45 examines whether a crossing of the level has been effected. If so, there is a return below the level, and the stage 46 establishes an end of peak, while consequently commanding the fraction collector to stop the sampling.

If the output of the test 45 is "no", the reason is that the signal has remained below the pilot signal, and outside a peak. In that case, the test 47 detects whether the slope of the detected signal is lower than the slope threshold $S\phi$. If this condition is achieved, at stage 48 the pilot signal continues to be established as a function of the detected signal and with the same slope as the latter, by the relation:

$$LEVEL = SIGNAL + L\phi$$

And a return is made to the stage 34. If, on the contrary, test 47 reveals that the slope of the signal is higher than the threshold $S\phi$, the "no" output of the test 47 is taken, and the LEVEL signal remains at its preceding value, whereafter a return is made to stage 34.

Reference will now be made to FIG. 4, which enables the present invention to be understood more clearly. In this figure, the abscissa represents an axis of the time, plotted in minutes, the ordinate representing a detection parameter. This is liquid phase chromatography performed with an elution gradient, the curve of the gradient being given in a chain line in relation to the Y-axis shown in the right-hand part of FIG. 4. It can be seen that at the start the percentage was 60% of B in A, then rising in a straight line to a fresh plateau at 70%, and thereafter again rising in a straight line as far as a final plateau at 80%.

A sample was injected at the moment O, and of course no significant peak was observed for a short time following the injection. At the same moment the value of the pilot LEVEL signal was fixed a little above the level of the baseline of the detected signal, this being shown by a light continuous line, while the LEVEL signal is shown by a heavier line.

At the start, the stages 35, 45, 47 and 48 in FIG. 3 are passed through. However, since the detected signal is constant, the LEVEL signal also remains constant.

A first sudden peak appears. At that moment the stages 35, 36 and 37 will be passed through, and the fraction collector is put into operation (apart from special programming of the peaks, as will be seen hereinafter).

For the following sample of the digital detected signal, the stages 35, 36, 38 and 40 "no" outputs will be passed through. The LEVEL signal therefore remains at a constant value, and we remain in the first peak. This will last until the value of the detected signal again becomes lower than the pilot LEVEL signal. At that moment the stages 34, 45 and 46 are passed through, this representing the end of a peak.

After peak 1 the LEVEL signal remains at its constant value, seeing that there is no deviation greater than $L\phi$ between the value of the detected signal and the value of the pilot signal. A very brief peak is removed by the fact that it remains lower than the pilot LEVEL signal.

After that we find a second peak 2. With this second peak, the same things take place as with the first peak. After the second peak it can be seen that the value of the pilot LEVEl signal will rise slightly, to follow an incipient rising of the baseline.

Such rising will be interrupted at the moment when a third peak appears, during which the value of the LEVEL signal once more remains constant.

After this third peak, the value of the pilot signal is re-established in accordance with the aforementioned relation:

$$LEVEL = SIGNAL + L\phi$$

It will be noted that the LEVEL signal continues to rise, following the slope of the baseline.

We continue in this way, detecting the fourth peak, then the fifth, then the sixth. After the sixth peak the baseline ceases to rise. It will be noted that the LEVEL signal will remain approximately parallel with the baseline—i.e., have approximately the same slope as the baseline. After the sixth peak, an artefact is again removed at that point.

We then find a seventh, followed by an eighth peak, both of them correctly detected.

During the further rise in the level of the baseline, the LEVEL signal will again follow the baseline, to detect finally the ninth and tenth peaks, whereafter no further significant peak appears.

It will be noted that the means according to the present invention operate remarkably well, very closely following the evolution of the baseline. The artefacts are suitably removed, while all the useful peaks are detected.

Of course, in practice the operator who is already acquainted, for example, with certain of the constituents, and wishes only to isolate others from them, can select, for example, the peaks for which he wishes to have a sampling at the fraction collector. This can be done by means of the keyboard 34. In this way, for example, only the peaks 1, 3, 5, 7 and 9 can be selected.

The horizontal chain dotted line is shown at a constant level, which might have been used in the prior art for a chromatograph of the kind illustrated in FIG. 4. This line of constant level would have correctly isolated peak 1, just caught peak 2, and correctly isolated peaks 3, 4 and 5. On the other hand, the fraction collector would then have been permanently energized, and would have sampled a large quantity of completely useless effluent, in which there would have been certain fitted tubes corresponding to the peaks 6, 7, 8, 9 and 10. Clearly this type of operation is quite unsatisfactory to the user.

FIG. 5 illustrates a different kind of chromatograph, provided with the means according to the invention, and having slightly different control systems. Operations take place in substantially the same way as in FIG. 4, so that FIG. 5 will not be described specially. It will merely be noted that the device according to the invention enables peaks which are not necessarily very pointed to be plotted with satisfactory accuracy.

We shall now refer to FIG. 6, which illustrates another application of the method according to the invention.

In this figure the widths of the peaks are also very considerable, and it will be observed at once that they are above the limit value of peak duration which occurs at stage 40 in FIG. 3.

At the start, therefore, the LEVEL signal is established at the value of the detected signal $+ L\phi$. This value rises slightly at the start of the first peak and remains constant during the whole of the first peak, which is detected in the same way as previously. However, when the stage 40 indicates that the duration of the peak has exceeded the maximum value, a transition is made to stage 41, which authoritively fixes the LEVEL signal at the value of the detected signal $+ L\phi$. This is the reason why we observe a very steep rise in the LEVEL signal, denoted by reference 61 in FIG. 6.

The LEVEL signal then follows in a substantially parallel manner (having regard to its digitalization) the evolution of the baseline. A fresh peak is detected somewhat later, during which the LEVEL signal remains at a constant value. At 63 the stage 38 detects a minimum in the detected signal. This detection is performed in known manner. A change of peak is then recorded at the level of stage 39, and the fraction collector passes on to another tube. When after this third peak the signal has a slope below the threshold, the value of the pilot signal then comes down again, with a slight delay, in accordance with stage 48, which refixes the LEVEL signal at the value of the detected signal+L$\phi$.

The examples just given show that the method according to the invention permits highly efficient operation in the analysis of eluents and their selection by a fraction collector, and that in the many cases in which the curve of the baseline of the detected signal varies to a considerable extent.

The invention covers not only the method which has just been disclosed, but also the means for putting it into effect, which can be incorporated in any effluent analysing device, more particularly in fraction detecting and/or collecting devices which can be used in liquid phase chromatography installations or other kinds of comparable installations.

Of course, the invention is not limited to the embodiment disclosed, but extends to any variant falling within the framework of the following claims. More particularly, the slope threshold can be defined (on the keyboard) in other ways than by a pre-established quantity (D%) and the value TMAX introduced by the operator.

We claim:

1. In a method of analysing effluents comprising the step of
   (a) detecting an electric signal comprising a baseline having peaks, certain of which represent useful information concerning the effluent, the detected electrical signal being representative of a physical and/or chemical property of the effluent as a function of time, and
   (b) analysing the detected electrical signal in order to select useful peaks of said detected electrical signal, the improvement wherein said step (b) of analysing the detected electrical signal comprises the following operations:
      (b1) defining a deviation value (L$\phi$) and defining a slope threshold value (S$\phi$)
      (b2) comparing the slope of the detected signal with the slope threshold value (S$\phi$)
      (b3) defining a pilot signal by summing up a value of the detected electrical signal and the deviation value (L$\phi$), if the slope of the detected electrical signal is lower than the slope threshold value (S$\phi$),
      (b4) limiting the evolution of the pilot signal when the slope of the detected signal is higher than the slope threshold value (S$\phi$), and
      (b5) selecting as a useful peak the consecutive values of the detected electrical signal which exceed the level of the pilot signal.

2. A method according to claim 1 characterized in that the operation (b4) of limiting the evolution of the pilot signal consists in stopping the evolution of the pilot signal when the slope of the detected electrical signal is higher than the slope threshold value (S$\phi$).

3. A method according to claim 1 characterized in that when the slope of the detected electrical signal becomes lower than the slope threshold value (S$\phi$) again the preceding value of the pilot signal is then resumed if the duration of exceeding the slope threshold value is less than a selected duration (TMAX), or in the contrary case, i.e. if the slope of the detected electrical signal exceeds the slope threshold value during a period of time superior to the selected duration (TMAX), a new value of the pilot signal is determined by summing up the detected electrical signal and the deviation value (L$\phi$).

4. A method according to claim 3, characterized in that the deviation value (L$\phi$) and the selected duration (TMAX) can be defined by the user, the slope threshold value (S$\phi$) being defined as the ratio between a pre-established quantity and the selected duration.

5. A method according to claim 1, characterized in that the passage of the detected electrical signal through a minimum is also detected, thus defining a change in useful peak.

6. A method according to claim 1, characterized in that the detected electrical signal is converted in digital form.

7. A method according to claim 1, characterized in that it also comprises the operation (c) consisting in sampling effluent at least once during a useful peak.

8. A method according to claim 1 characterized in that the effluent is the liquid leaving a liquid phase chromatography column.

9. A method according to claim 8, characterized in that the column is fed with a elution gradient.

10. A device for analysing effluents comprising
    (a) means for detecting an electric signal comprising a baseline having peaks, certain of which represent useful information concerning the effluent, the detected electrical signal being representative of a physical and/or chemical property of the effluent as a function of time, and
    (b) means for analysing the detected electrical signal in order to select useful peaks of said detected electrical signal, the improvement wherein said means for analysing the detected electrical signal comprises:
       (b1) means for defining a deviation value (L$\phi$) and means for defining a slope threshold value (S$\phi$)
       (b2) means for comparing the slope of the detected signal with the slope threshold value (S$\phi$),
       (b3) means for defining a pilot signal by summing up a value of the detected electrical signal and the deviation value (L$\phi$), if the slope of the detected electrical signal is lower than the slope threshold value (S$\phi$),
       (b4) means for limiting the evolution of the pilot signal when the slope of the detected signal is higher than the slope threshold value (S$\phi$),
       (b5) means for selecting as a useful peak the consecutive values of the detected electrical signal which exceed the level of the pilot signal.

* * * * *